March 15, 1960 SAMUEL R. FUJIMOTO Plant Pat. 1,920
SALMON ROSE VERBENA PROSTRATE PLANT
Filed March 19, 1959
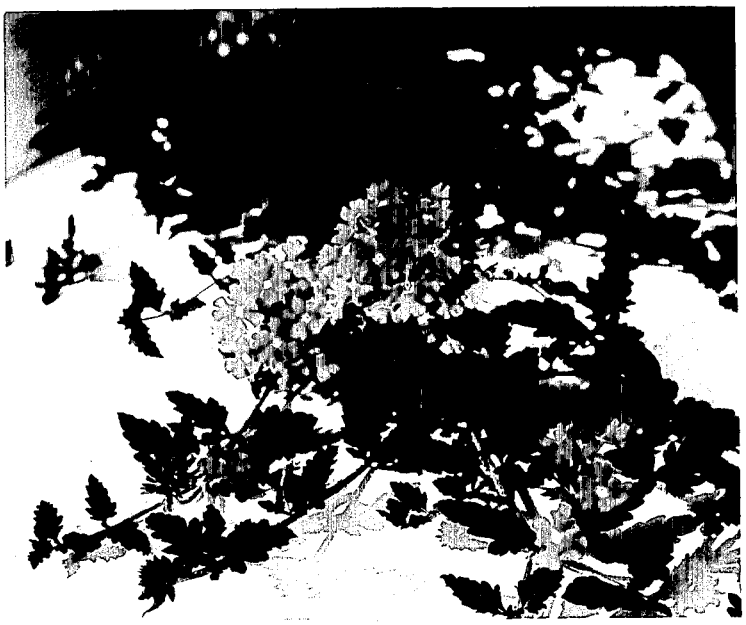
SAMUEL I. FUJIMOTO,
INVENTOR.
HERZIG & JESSUP,
ATTORNEYS.
BY Albert M. Herzig United States Patent Office Plant Pat. 1,920
Patented Mar. 15, 1960

1,920

SALMON ROSE VERBENA PROSTRATE PLANT

Samuel R. Fujimoto, Gardena, Calif.

Application March 19, 1959, Serial No. 800,610

1 Claim. (Cl. 47—60)

This invention provides a new and distinct variety of salmon rose verbena plant. The plant is of the Peruviana-Verbena type, as listed in Bailey's Hortus Second. The new variety of plant is particularly characterized by its unique salmon rose flowers, which are large, forming large clusters of many flowers. The plant is of the ground-cover type. It is of the hanging, or prostrate type, being distinctly different from the known Peruviana-Verbena type. It has relatively large foliage. The stems are larger, with the leaves having more space between them. The branches, runners or tendrils hang down and have little nipples underneath them which take root upon engaging the ground.

The new variety has been reproduced asexually at 15913 South Main Street, Gardena, California, from slips and cuttings over several generations and the characteristics appear to be fixed. The new plant is a sport which was discovered in a cultivated bed of Peruviana-Verbena at the site of a residence in Gardena, California.

The new plant, reproduced as stated, by slips and cuttings, shows a habit, prostrate in character and vigorous and hardy in growth. The plant has shown definite resistance to mildew; no trace of mildew has been found in these plants to date which is a characteristic of the ordinary Peruviana-Verbena (scarlet flower).

The accompanying drawing shows a typical specimen flower, and some of the foliage of the new variety depicted in color as nearly true as it is reasonably possible to make the same in a color illustration of this character.

*Flowers*

The salmon rose color of the flowers is distinct from all other verbena flowers. According to Maerz and Paul Dictionary of Color, the flowers are salmon rose in color. The individual flowers are approximately ½ inch in diameter and an average of about 30 flowers form clusters which measure about 2 inches in diameter and about 1½ inches in axial length. The young flowers have a small yellow eye which is not so pronounced in the older flowers. The individual stems are about ⅛ inch in diameter and are variable in length.

*Leaves*

The leaves are thick and dark green, generally about 1 inch in diameter and 2 inches in length near the base, while leaves at the tips of branches are smaller. Foliage is relatively large. The stems are larger, having more space between the leaves, and the plant is of the hanging or prostrate type appropriate as ground cover vegetation. The branches, runners or tendrils hang down and have little nipples underneath them and take root upon reaching the ground, i.e., they are self-rooting.

*Seed*

No seeds have been obtained; the plants have been reproduced only by means of vegetative cuttings and slips.

*General*

The plant is a prostrate type. Its vegetative habits and growth are vigorous and it shows promise as ground cover vegetation. Its blooming habit is similar to the Peruviana-Verbena from about April to October. The color of the cluster of flowers varies from the perimeter toward the center, being more red toward the center of the cluster. The variation in color, according to Maerz and Paul Dictionary of Color, corresponds to the variation from Plate 2, L6 to K3. The older blossoms tend to lighten in color. The foliage is relatively large. The stems are larger than the ordinary Peruviana-Verbena. The plant is self-rooting.

I claim:

A new and distinct variety of salmon rose verbena plant substantially as illustrated and described, characterized by individual flowers of salmon rose color in large clusters of many flowers borne on long thick prostrate stems, by large thick dark green leaves, widely spaced on the stems and by good vigor, the flowers having darker areas toward the center of rose color.

No references cited.

UNITED STATES PATENT OFFICE

CERTIFICATE OF CORRECTION

Plant Patent No. 1,920 March 15, 1960

Samuel R. Fujimoto

It is hereby certified that error appears in the above numbered patent requiring correction and that the said Letters Patent should read as corrected below.

In the drawing, lower right-hand corner, name of inventor, for "Samuel I. Fujimoto" read -- Samuel R. Fujimoto --.

Signed and sealed this 25th day of October 1960.

(SEAL)
Attest:

KARL H. AXLINE
Attesting Officer

ROBERT C. WATSON
Commissioner of Patents